(12) United States Patent
Safraoui

(10) Patent No.: US 10,695,451 B2
(45) Date of Patent: Jun. 30, 2020

(54) UVC DECONTAMINATION AND DETOXIFICATION DEVICE

(71) Applicant: HEALTHY PULSE, Evry (FR)

(72) Inventor: Georges Safraoui, Villejust (FR)

(73) Assignee: HEALTHY PULSE, Evry (FR)

( * ) Notice: Subject to any disclaimer, the term of this patent is extended or adjusted under 35 U.S.C. 154(b) by 377 days.

(21) Appl. No.: 15/329,032

(22) PCT Filed: Jul. 22, 2015

(86) PCT No.: PCT/EP2015/066730
§ 371 (c)(1),
(2) Date: Jan. 25, 2017

(87) PCT Pub. No.: WO2016/012488
PCT Pub. Date: Jan. 28, 2016

(65) Prior Publication Data
US 2017/0209607 A1    Jul. 27, 2017

(30) Foreign Application Priority Data
Jul. 25, 2014    (FR) ..................... 14 57205

(51) Int. Cl.
| A61L 2/10 | (2006.01) |
| A23L 3/28 | (2006.01) |
| A23B 7/015 | (2006.01) |
| A23L 5/30 | (2016.01) |
| A61L 2/26 | (2006.01) |

(Continued)

(52) U.S. Cl.
CPC ............. *A61L 2/10* (2013.01); *A23B 7/015* (2013.01); *A23L 3/28* (2013.01); *A23L 5/36* (2016.08); *A61L 2/26* (2013.01); *G02B 5/0891* (2013.01); *H01J 61/52* (2013.01); *H05B 41/39* (2013.01); *A23V 2002/00* (2013.01); *A61L 2202/11* (2013.01); *A61L 2202/14* (2013.01); *A61L 2202/25* (2013.01)

(58) Field of Classification Search
None
See application file for complete search history.

(56) References Cited

U.S. PATENT DOCUMENTS

| 5,405,631 A | 4/1995 | Rosenthal | |
| 5,768,853 A * | 6/1998 | Bushnell | A23L 3/26 |
| | | | 53/141 |

(Continued)

FOREIGN PATENT DOCUMENTS

| EP | 1547538 A1 | 6/2005 |
| EP | 1749494 A2 | 2/2007 |
| WO | 2013/106077 A2 | 7/2013 |

OTHER PUBLICATIONS

Apr. 28, 2016 International Search Report issued in International Patent Application No. PCT/EP2015/066730.

(Continued)

*Primary Examiner* — Andrew Smyth
(74) *Attorney, Agent, or Firm* — Oliff PLC

(57) ABSTRACT

A device for decontamination and detoxification by emitting light flashes rich in UV radiation, particularly UVC. The device includes: a flash lamp; a reflector, preferably placed behind the flash lamp, so as to reflect the light emitted by the lamp towards an output window; and a UV detector for measuring the UV radiation emitted by the lamp.

25 Claims, 7 Drawing Sheets

(51) Int. Cl.
*G02B 5/08* (2006.01)
*H01J 61/52* (2006.01)
*H05B 41/39* (2006.01)

(56) References Cited

U.S. PATENT DOCUMENTS

| | | | |
|---|---|---|---|
| 6,132,784 A | 10/2000 | Brandt et al. | |
| 6,566,659 B1* | 5/2003 | Clark | A23L 3/26 |
| | | | 250/453.11 |
| 6,680,028 B1* | 1/2004 | Harris | A61L 9/16 |
| | | | 422/122 |
| 7,498,004 B2* | 3/2009 | Saccomanno | A61L 2/10 |
| | | | 422/306 |
| 2003/0147770 A1* | 8/2003 | Brown | A61L 2/0011 |
| | | | 422/24 |
| 2003/0155531 A1* | 8/2003 | Clark | A23L 3/26 |
| | | | 250/492.1 |

OTHER PUBLICATIONS

Apr. 28, 2016 Written Opinion issued in International Patent Application No. PCT/EP2015/066730.

* cited by examiner

UVC DECONTAMINATION AND DETOXIFICATION DEVICE

The present invention relates to installations for emitting flashes rich in UV radiation, for decontaminating or detoxifying surfaces, for example the skins of foods such as fruit or vegetables. The detoxification operation is intended to considerably reduce certain mycotoxins such as patulin. Patulin is a toxic substance resulting from the metabolism of certain molds present on fruit and vegetables.

UV radiation, and more particularly UVC radiation (180-280 nm), has a powerful biocidal action on potentially pathogenic or undesirable agents such as bacteria, viruses, fungi, yeasts, and the like, or on toxic agents such as patulin.

Accordingly, UV radiation sources based on flash lamps have been proposed for use.

In order to be effective, the flashes must carry a large amount of energy, giving rise to problems in terms of the dissipation of the calorific energy generated and the durability of the materials used.

Moreover, in some situations the flash lamps may fail to emit sufficient energy, for example because of an accidental short circuit causing the electric arc to be created outside, or only partially inside, the lamp; the radiation may also be unsuitable because of the aging of the lamp, which tends to opacify the quartz envelope used for the lamp. At the present time, the measurement of the current generated toward the lamp does not ensure that a flash has actually been emitted, or that the necessary UVC dose has been produced.

There is also a need to ensure the traceability of the UV emissions, notably in order to guarantee that decontamination or detoxification treatment has actually taken place.

The invention is intended, notably, to meet this need and to improve UV radiation generation installations.

This is achieved, according to a first aspect of the invention, by means of a device for decontamination by emission of light flashes rich in UV radiation, notably UVC radiation, comprising:
  a flash lamp,
  a reflector, notably one placed behind the flash lamp, to redirect the light emitted by the lamp toward an output window, and
  a UV detector for measuring the UV radiation emitted by the lamp.

Because of the presence of the UV detector, it is possible to know the level of UV radiation that is actually emitted. Thus, it is possible to check that the flash has actually taken place, and, on the other hand, to ensure that the level of UV generation matches the expected level.

The reflector may have an opening, and the UV detector may be placed behind this opening. This enables the UV detector to be fully integrated into the installation and enables a UV detector to be associated with each flash lamp used. The UV detection may be carried out closer to the lamp, thus providing a reliable image of the emitted radiation.

The diameter of the opening is preferably less than or equal to 5 mm, or more preferably between 0.75 and 1.25 mm, being 1 mm for example.

Many industrial applications require a sealed optical head. In this case, the output window may comprise a UV-transparent panel, preferably made of synthetic quartz, and preferably assembled by gluing onto a support frame at its periphery. Monitoring any breakage of this panel becomes a major safety factor in many food-related applications.

The panel is preferably coated on its periphery with a first metallized track extending along at least one longer side of the panel.

This first track may extend in the form of an open loop, whose ends are preferably located on a shorter side of the panel. The metallized track may then be connected electrically to an electrical continuity detector, and may be used to detect any cracking in the panel. This is because such cracking will interrupt the electrical conduction of the track, which may be detected by the electrical continuity detector. To ensure the breaking of this conductive track, its thickness is preferably less than 100 µm, more preferably less than 10 µm, or even more preferably less than 1 µm. The metallic track may be covered on its outer face with an electrical insulating coating, notably a silica coating, which may have been vacuum deposited. This reduces the risk of disturbing the reading of the conductivity of the track. The track preferably faces toward the flash lamp.

A second track, with no constraint on its thickness, may be deposited on the outer side of the panel. It may thus be superimposed on an adhesive joint used for assembling the panel and support frame. This second track may then form a screen against the incident UV radiation to protect this adhesive joint. This may prevent premature aging of the joint under the action of the UVC.

An advantageous solution is to combine both functions, namely that of monitoring the breakage of the panel, and that of protecting the adhesive joint against the UV emitted by the lamp, within the same track. The track must then be thin enough to ensure that it breaks if there is a break in the panel, while preferably having a thickness of at least 100 nm of metal in order to block the UV radiation toward the panel, and preferably being positioned on the same side as the joint.

The support frame may be assembled onto a casing containing the reflector, with the interposition of a seal.

The UV detector is preferably carried on an electronic circuit card provided above the reflector.

The device may comprise a radiator supporting the reflector, this radiator having grooves which are formed between fins and accommodate tubes for the circulation of a cooling liquid, notably water.

The tubes are preferably retained by clamps fitted between the fins. It is advantageous to avoid gluing or rigidly fixing the tubes to the radiator, in order to allow them to move slightly, and to be correctly positioned if necessary, relative to the radiator.

The reflector is preferably fixed on the radiator body with the interposition of a heat-conducting sheet. This enables the heat given off by the lamp to be distributed correctly over the whole length of the radiator.

The tubes may be inserted at their ends into manifolds having seals, preferably O-rings, fitted on the tubes.

The manifolds may also accommodate the ends of the flash lamp.

The flash lamp may be accommodated in a quartz envelope, engaged in the manifolds.

The device preferably comprises a control circuit which stores a log of the UV emission of the flashes, based on the radiation detected by the UV detector.

In another aspect, the invention also proposes, independently or in combination with the above, a UV generating device, comprising:
  a flash lamp,
  and a panel through which the flashes are emitted, the panel carrying a conductive track forming an open loop and connected to an electronic circuit enabling any breakage of the panel to be detected from a break in the electrical continuity of said track.

In another aspect, the invention also proposes, independently or in combination with the above, a UV generating device, comprising:
- a flash lamp,
- and a panel through which the flashes are emitted, the panel being glued by an adhesive joint to a support frame, the panel carrying at its periphery a metallic track superimposed on the adhesive joint and protecting the latter from the UV radiation emitted by the lamp.

In another aspect, the invention also proposes, independently or in combination with the above, a UV generating device, comprising:
- a flash lamp,
- a reflector for redirecting the light emitted by the flash lamp toward an output window,
- a radiator for supporting the reflector, the radiator having a body with fins, and tubes between the latter, in which a cooling liquid circulates, the tubes being pressed against the body of the radiator, preferably by clamps, and being accommodated freely at their ends in manifolds, with the interposition of an O-ring between the tube and the manifold at the ends of each tube.

All the additional characteristics mentioned in the description of the first aspect of the invention are equally valid for these other aspects.

According to another of its aspects, the invention also proposes the use of a device according to the invention for destroying pathogenic or undesirable agents such as bacteria, viruses, fungi or yeasts, or for destroying toxic agents such as patulin. Thus food, notably fruit or vegetables, may be exposed to the UV radiation, for example before being processed into purees or stewed fruit.

The food may be moved by being driven in rotation under the installation.

The dose of UV radiation emitted by the corresponding lamp may advantageously be measured at each flash, using the aforesaid UV detector. Preferably, information related to the UV emission of each flash is stored, together with the number of flashes produced.

The energy sent to the lamp may be modified on the basis of the previously measured radiation emitted by the lamp, to compensate for the variation of the emission characteristics caused by the aging of the lamp.

The electrical continuity of the aforesaid track may advantageously be measured, preferably before and/or after the emission of each flash, in order to detect the state of the panel.

Preferably, in order to obtain a toxin reduction by a factor of at least 2, preferably at least 10, or more preferably more than 100, provision is made to ensure that:
- the object to be treated is rotated through at least 360°, in order to treat the whole surface of the object; the frequency of the flashes is such that, during the minimum rotation of 360° of the object to be treated, there is at least 1 flash for every 180°, or preferably at least one flash for every 120°, and/or
- at a distance of 10 cm, the optical head delivers a dose (or energy density) of between 1 and 3 joule/cm$^2$, and/or
- at a distance of 10 cm, the optical head delivers a power density of between 2 kW/cm$^2$ and 15 kW/cm$^2$, and/or
- the emitted light flash is rich in UVC, that is to say has a spectral distribution such that at least 20% of the energy is between 200 nm and 315 nm.

The invention also proposes a method for destroying pathogenic agents present on the surfaces of objects such as fruit or vegetables, and notably for destroying patulin, comprising the steps of:
- causing the objects to be treated to rotate through at least 360°,
- subjecting the surfaces of the objects thus rotated to the UVC-rich light emitted by one or more flash lamps, the energy density of the flash or flashes being such that the surfaces of the objects are exposed to an energy density of at least 1 J/cm$^2$ and to a power density of at least 2 kW/cm$^2$, and that at least 20% of the received energy is between 200 and 315 nm.

In order to cause the objects to rotate, they may be carried under the light emission window or windows by a conveyer comprising rollers which move with the objects and on which the objects rest, the rollers being caused to rotate at least when they pass under said windows. In particular, the rollers may come into contact with a friction strip which causes them to roll on the latter. In a variant, the rollers are fixed to toothed wheels which engage with a chain or a toothed belt extending under the emission window or windows. The treated objects may be apples. The surface which causes the rollers to rotate may be stationary, in which case the rotation speed of the rollers is governed by their speed of movement, or movable, in which case the rotation speed of the rollers can be precisely controlled.

The flashes may cause the generation of ozone inside the enclosures containing the lamps.

The ozone thus generated may damage some materials when it comes into contact with them. For example, the reflector, if made of aluminum, may become oxidized and generate alumina in the form of a fine powder which is deposited on the panel and progressively obscures the light.

Advantageously, an oxygen absorber is placed in each enclosure, to purge the oxygen from the air and reduce the ozone formation.

Thus a container, in the form of a sachet for example, is installed in the enclosure, preferably in an area not directly exposed to the light of the flash lamp, this container holding a substance capable of reacting with the atmospheric oxygen to eliminate this from the enclosure.

The substance is provided in a sufficient quantity to convert all the oxygen initially present in the volume of the enclosure, and to maintain a reduced level of oxygen in the enclosure during the desired period, given that there may be minor leaks.

The substance is renewed on each maintenance operation.

The substance is in powder form, for example, packaged in sachets.

The substance may be based on iron, notably iron carbonate, which reacts by the reaction $4\ FeCO_3 + 6\ H_2O + O_2 \rightarrow 4\ Fe(OH)_3 + 4\ CO_2$.

Such a substance also has the advantage of absorbing atmospheric humidity and generating $CO_2$ which prevents a pressure drop in the enclosure.

It is also possible to add a special moisture absorber such as a silica gel.

A non-ferrous oxygen absorber, such as an ascorbate or sodium bicarbonate, may be used.

The sachets containing the oxygen absorbent substance may be placed in a perforated metal basket in contact with the substance contained in the enclosure.

The invention will be made clearer by the perusal of the following detailed description of non-limiting exemplary embodiments thereof, and the examination of the attached drawing, in which.

Figure 1:
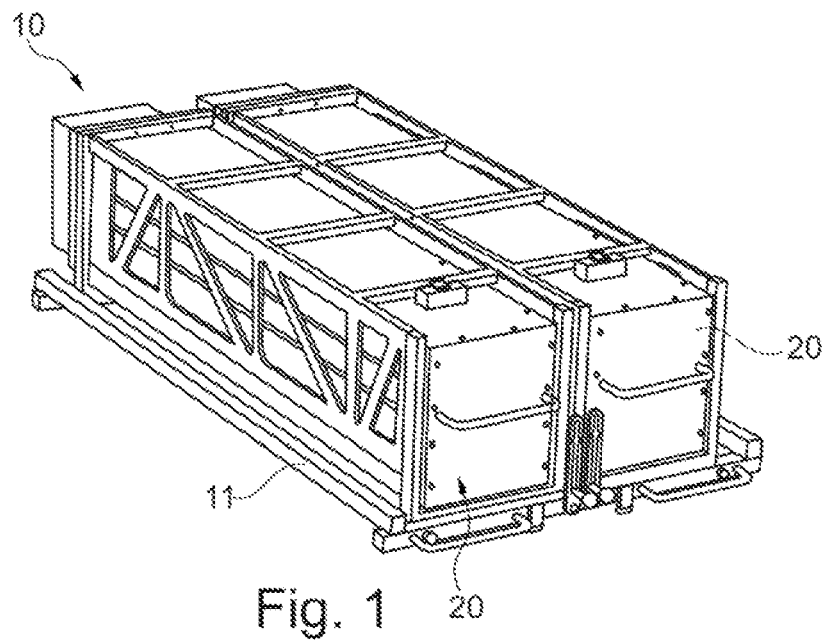
FIG. 1 shows in a schematic and partial manner, and in perspective, a treatment installation according to the invention.

FIG. 1 shows part of a decontamination installation 10 according to the invention, comprising a frame 11 on which are fixed one or more optical units 20, two of these units being shown in the illustrated example.

Food or other products to be decontaminated is moved under the optical units 20, using any suitable conveyer. In a variant, the installation is arranged to emit the UV radiation toward a surface to be decontaminated, which is, for example, the floor or the wall of a room.

The installation 10 comprises an electrical power supply (not shown), for supplying power to each optical unit 20.

The installation 10 also comprises means for cooling by circulation of a liquid, preferably water.

Figure 2:
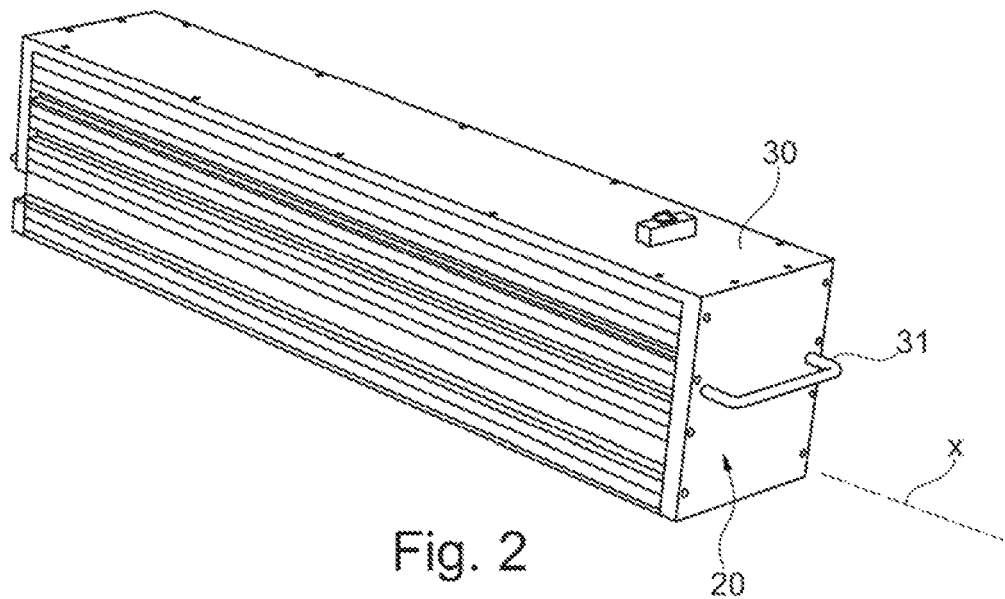
FIG. 2 shows in isolation, in perspective, an optical unit of the installation of FIG. 1.

Each of the optical units 20 advantageously has, as shown in FIG. 2, a shape which is elongated along a longitudinal axis X, and each unit may have a casing 30 provided at the front end with a handle 31 to facilitate its positioning on the frame 11 and its removal therefrom.

Figure 3:
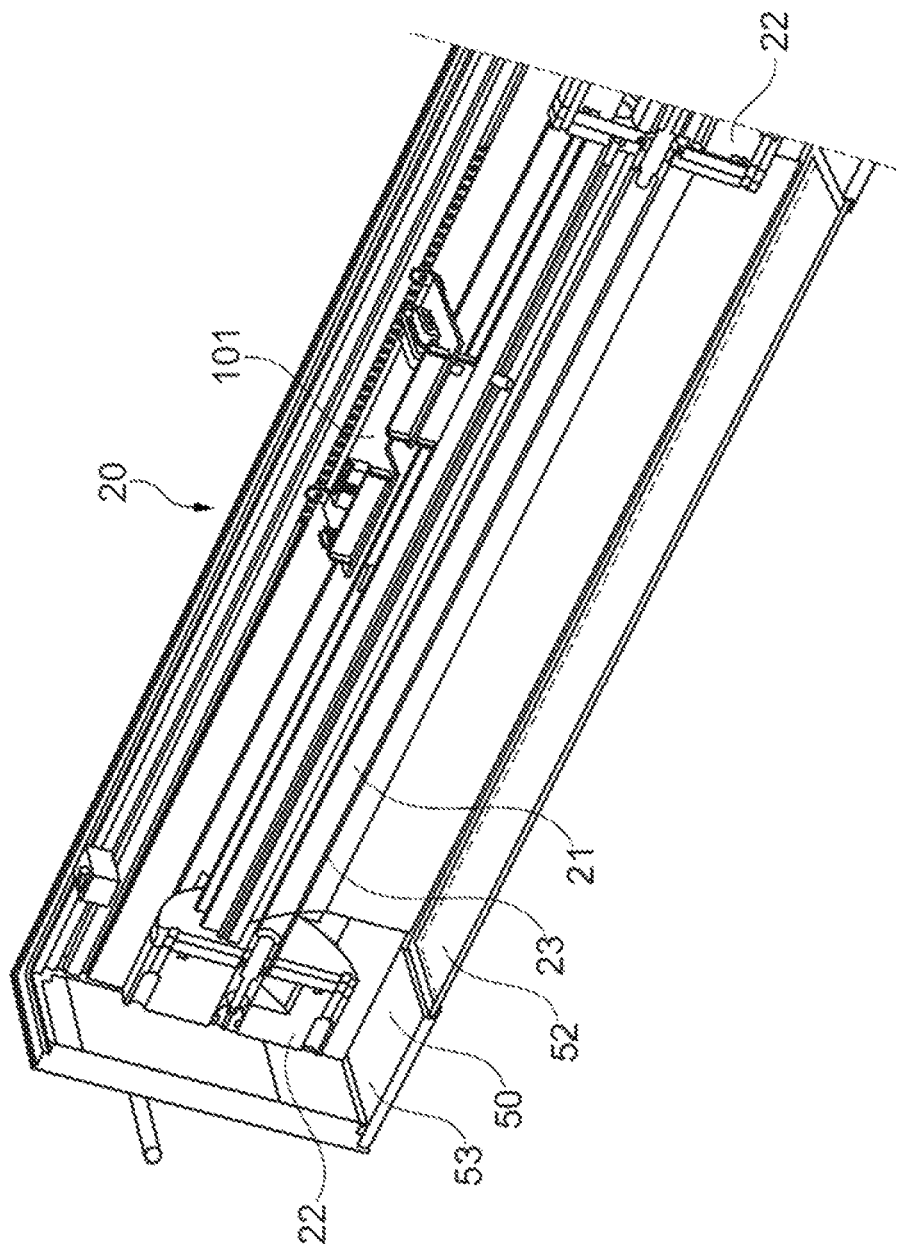
FIG. 3 shows, in partial and schematic longitudinal section, the optical unit of FIG. 2.

If reference is made to FIG. 3, it will be seen that each optical unit 20 comprises a flash lamp 21, preferably rectilinear with an axis X, the ends of which are accommodated in manifolds 22.

The lamp 21 extends inside an envelope 23 in the form of a quartz sleeve, which defines a space around the lamp in which the cooling liquid may circulate.

Figure 4:
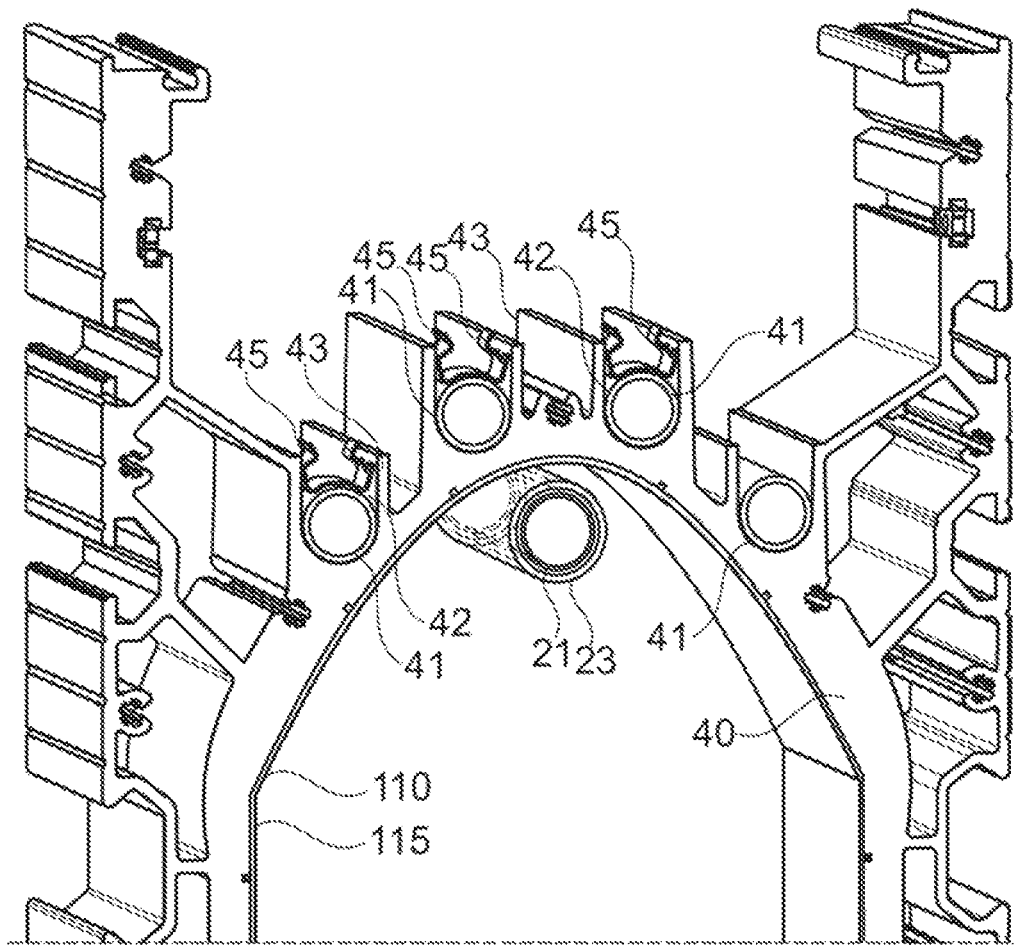
FIG. 4 is a partial and schematic cross section of the optical unit.
Figure 5:
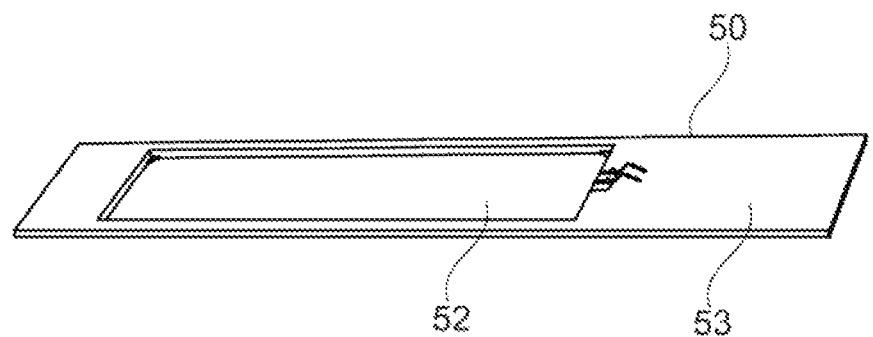
FIG. 5 shows, in isolation, the cover plate of the optical unit.

As is shown in greater detail in FIG. 4, the unit 20 comprises a radiator 40 on which are fixed tubes 41, through which the cooling liquid also passes. This radiator 40 supports a reflector 110 on the same side as the lamp.

The reflector 110 may be formed by an aluminum sheet polished on the face turned toward the lamp 21, and coated on this face with a layer of quartz which protects it from oxidation. The reflector may be polished electrolytically.

A sheet 115 of a highly thermally conductive material, preferably a ceramic filled film, having a thermal conductivity greater than or equal to 2 W/m·K, is interposed between the reflector 110 and the radiator 40.

The tubes 41 are accommodated in grooves 42 formed between the fins 43 of the radiator 40, the semi-circular cross sections of the bottoms of the grooves being adapted to the diameter of the tubes.

Preferably, the tubes 41 are held in the radiator 40 without adhesive, thus facilitating assembly and maintenance.

In particular, the absence of adhesive permits higher assembly tolerances on the insertion of the tubes 41 into the manifolds 22.

A thermally conductive compound is preferably placed in the grooves 42, to improve thermal conduction between the tubes 41 and the radiator 40.

Figure 10:
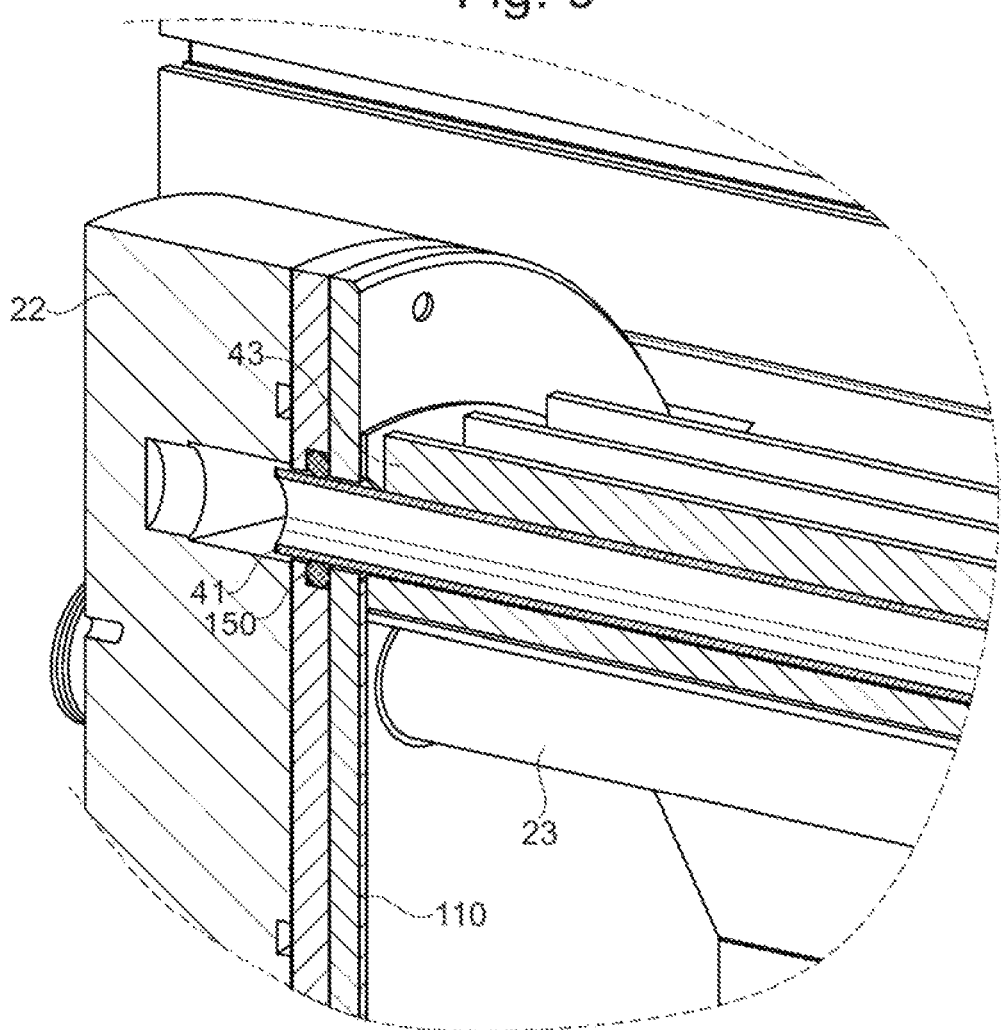

As shown in FIG. 10, the ends of the tubes 41 are accommodated in the manifolds 22, which provide the necessary interconnections for the supply of cooling liquid to the tubes. O-rings 150 may be fitted to the tubes 41 for this purpose.

The tubes 41 may be held in the corresponding grooves 42 by clamps 45 which bear on the fins 43. These clamps 45 may be put in place after the installation of the tubes 41 in the manifolds 22.

In operation, the cooling liquid circulates in parallel in the tubes 41 and in the enclosure 23.

The casing 30 is closed by a cover plate 50 on its lower part.

The plate comprises a panel 52 and a support frame 53 of opaque material, for example metal. The panel 52 is preferably made of synthetic quartz, and its thickness may be between 1.5 and 5 mm, for example 2 mm.

The frame 53 defines a window delimited by an edge of reduced thickness 55, on which the panel 52 is fixed by means of an adhesive 56.

Figure 6:
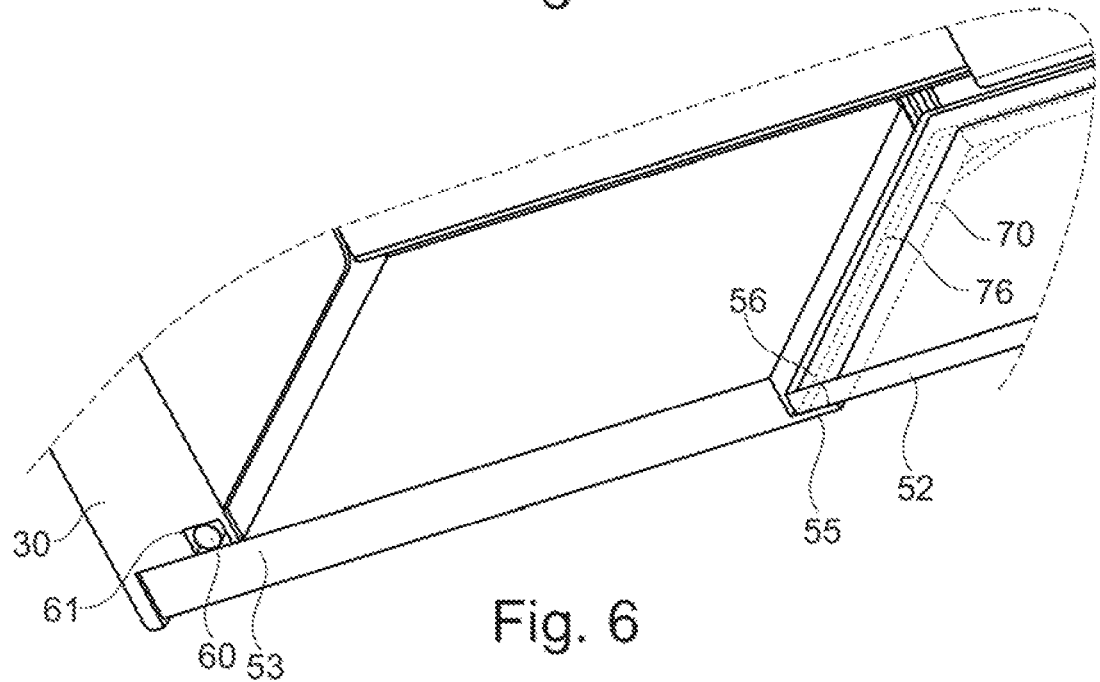
FIG. 6 shows a detail of the mounting of the cover plate on the casing of the optical unit.
Figure 7:
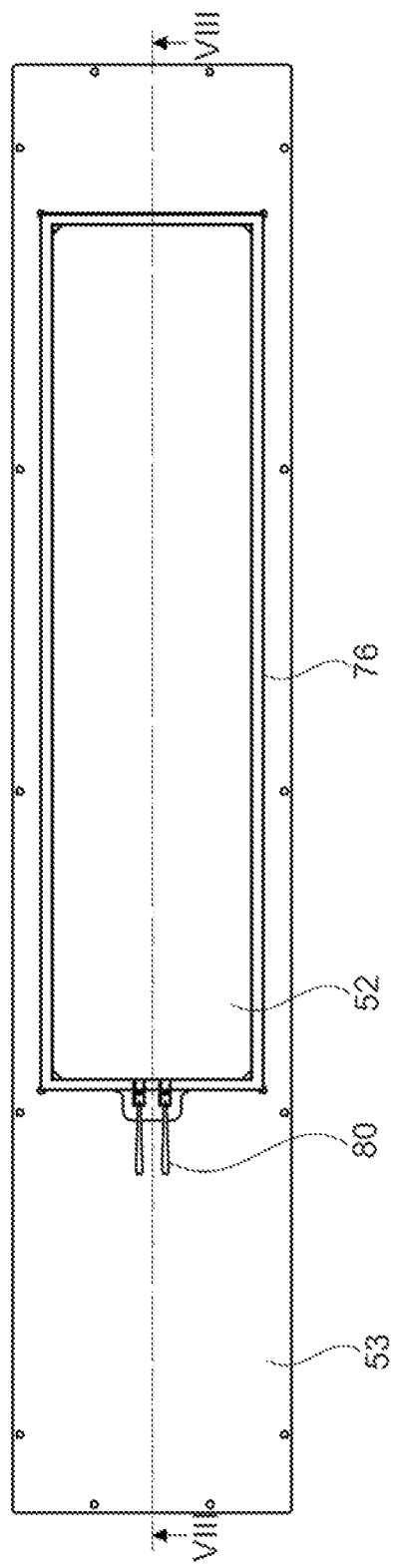
FIG. 7 shows a top view of the cover plate.
Figure 8:
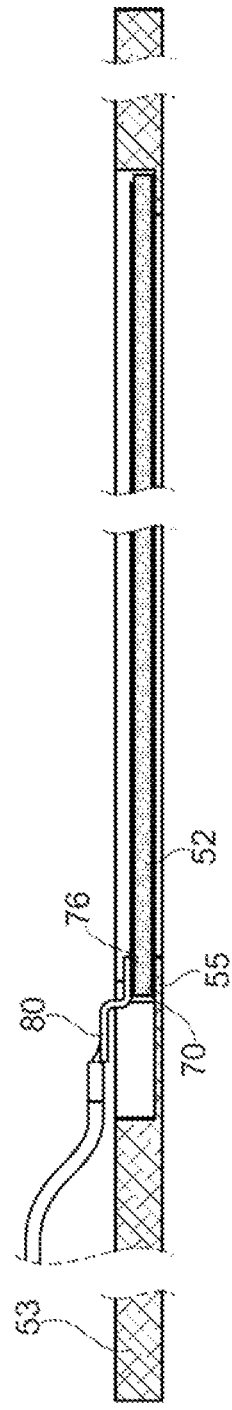
FIG. 8 is a longitudinal section along the line VIII-VIII of FIG. 7.
Figure 9:
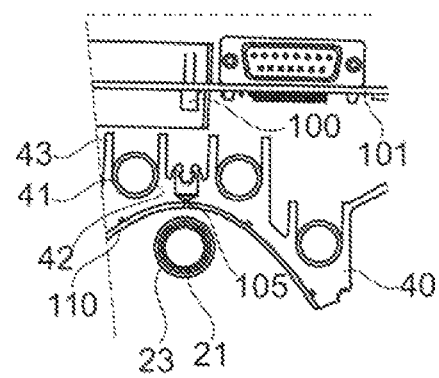
FIGS. 9 and 10 show details of the construction of the reflector.

A seal 60 may, as shown in FIG. 6, be accommodated in a groove 61 of the casing 30, and may bear on the periphery of the frame 53.

In order to protect the adhesive from the UV radiation emitted by the flash lamp, the panel 52 carries a first metallic track 70 which forms a screen against this radiation. The first track 70 is located on the face of the panel 52 which is turned toward the outside. The metal of the first track is preferably aluminum, preferably with a thickness of at least 100 nm. The first track is sufficiently wide to protect the whole of the adhesive, having a width of several mm for example, notably between 4 mm and 6 mm, and extends along the whole periphery of the panel. The adhesive 56 extends between the first track 70 and the edge 55.

In the illustrated example, the panel 52 also carries a second metallic track which forms an open loop on the periphery of the inner face, turned toward the flash lamp.

Contacts 80 may be soldered onto the second track 76. This track is preferably coated, except in the contact soldering area, with a layer of an electrical insulator such as silica, to prevent any soiling or other contact with any metal covering the second track from falsifying the conductivity measurement.

The second track 76 is, for example, narrower than the first, with a width of 4.5 mm, for example.

In the example considered here, the first and second tracks are located on opposite faces of the panel 52, but in a variant both tracks may be located on the same side if the first is electrically insulated from the second.

If there is a crack in the panel 52, the conduction of the second track 76 between the contacts 80 is interrupted, and this may be detected electrically by a suitable electronic circuit.

It is then possible to interrupt the emission of the flashes and/or to indicate the anomaly.

The optical unit 20 comprises a UV radiation detector 100, mounted on a printed circuit 101 which is fixed relative to the radiator 40.

The detector 100 receives the radiation emitted by the lamp 21 through an opening 105 which passes through the radiator 40 and the reflector 110. The opening 105 is, for example, 1 mm in diameter.

The distance between the entry to the opening 105 on the side of the lamp 21 and the detector 100 is, for example, between 1.5 and 2.5 cm.

The detector 100 can be used in order to discover the amount of UVC emitted at each flash and to check that the optical unit 20 is actually emitting the desired dose.

The detector 100 is preferably based on a photodiode, preferably made of AlGaN (aluminum gallium nitride), to obtain a significant gain in the UVC band.

The installation 10 may comprise an electronic circuit which adjusts the supply parameters of the lamp 21 in order to compensate for the deterioration of the lamp. For example, if the lamp tends to become obscured, the current strength may be increased in order to emit more UV radiation.

The installation may be arranged to store the amount of UVC emitted at each flash, to enable any failure to be detected, and to provide traceability of the decontamination performed.

The installation may comprise a system for cleaning the outer side of the panel 52 by a pressurized water spray.

The invention is not limited to the example described above. In particular, the shape of the reflector or of the radiator may be modified without departing from the scope of the present invention.

The invention is advantageously applicable to the treatment of fruit or vegetables, notably apples, for example in order to eliminate patulin or other mycotoxins present on their surfaces.

The installation according to the invention advantageously comprises means for treating the whole surfaces of the fruit or vegetables, by making the fruit or vegetables perform at least one rotation about themselves during their passage under the treatment heads which emit the UVC-rich flashes.

Figure 11:
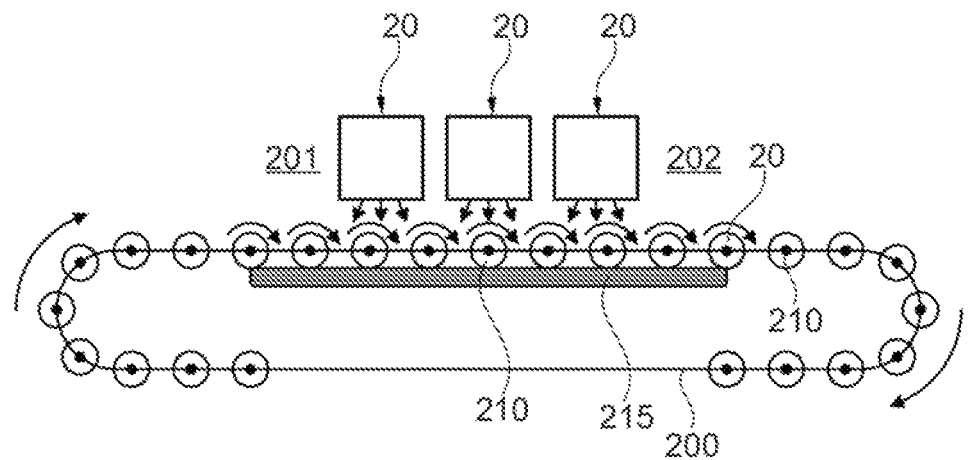
FIGS. 11 and 12 show in a schematic manner two examples of conveyers that may be used.

FIG. 11 shows a first example of an installation of this type. This comprises a conveyer 200 which revolves in a closed loop and passes in front of the treatment heads 20, of which there are three, for example. The products to be treated are placed on the conveyer 200 at 201, upstream of the treatment heads, and are retrieved downstream of the heads, at 202.

The conveyer 200 comprises rollers 210 on which the products to be treated rest.

A friction strip 215 extends at the position of the treatment heads and slightly upstream and downstream of them, and the rollers 210 come into contact with this strip. The friction strip 215 causes the rollers 210 to revolve about themselves at the position of the treatment heads, thereby causing the products to rotate. The diameter of the rollers is chosen so that the products perform at least one rotation about themselves during their passage under the treatment heads 20, thus receiving a plurality of UVC-rich flashes, which in combination reach substantially the whole surface of the products.

In the example shown in FIG. 11, the friction strip 215 is fixed. It may also be replaced with a belt made to rotate in the opposite direction to the advance of the conveyer 200, so as to drive the products to be treated at the desired rotation speed, appropriate for the treatment to be performed.

Figure 12:
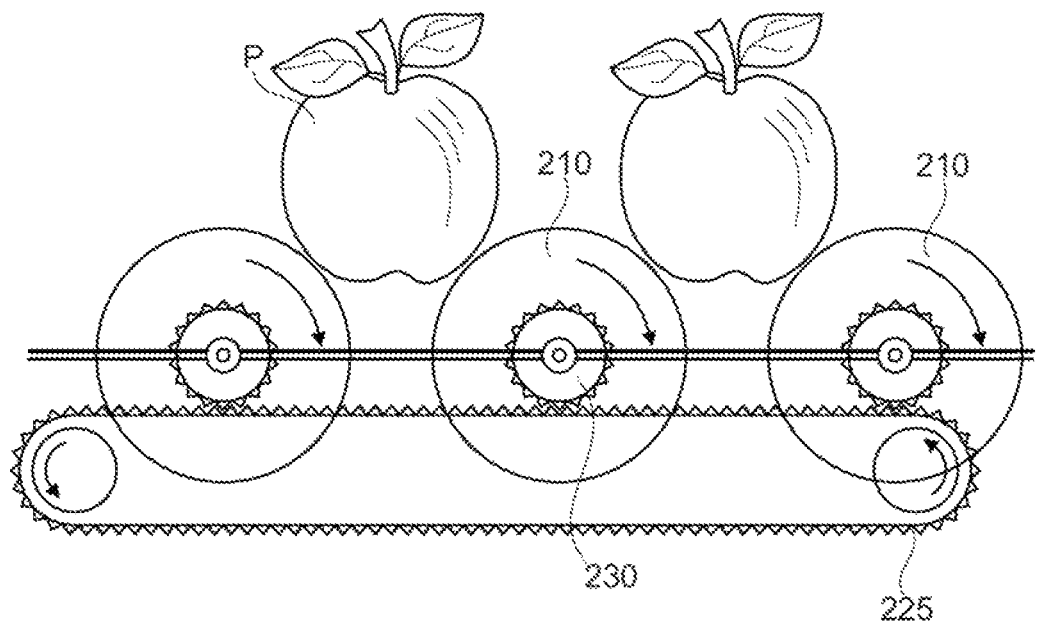

In the variant of FIG. 12, each of the rollers 210 is fixed to a pinion 230, and a chain or toothed belt 225 engages with each pinion 230 under the treatment heads 20, to drive the corresponding roller 210 at the desired rotation speed. Preferably, this chain or toothed belt moves in the opposite direction to the rollers 210, so that their speed relative to one another may be increased.

Advantageously, as mentioned above, an oxygen absorber is placed in the enclosure containing the lamp.

The expression "comprising a" is to be understood as being synonymous with "comprising at least one", unless specified otherwise.

The invention claimed is:

1. A device for decontamination and detoxification by emission of light flashes rich in UV radiation, comprising:
   a flash lamp,
   an output window placed in front of the flash lamp, the output window comprising a panel, the panel being assembled at a periphery of the panel onto a support frame and coated on the periphery of the panel with at least one metallic track extending along at least one longer side of the panel, the metallic track extending in the form of an open loop and being electrically connected to an electrical continuity detector,
   a reflector placed behind the flash lamp to redirect the light emitted by the lamp toward the output window, and
   a UV detector for measuring the UV radiation emitted by the lamp.

2. The device as claimed in claim 1, wherein ends of the open loop are located on a shorter side of the panel.

3. The device as claimed in claim 1, wherein the metallic track is superimposed on an adhesive joint used for the assembly of the panel and the support frame, the metallic track forming a screen against the incident UV radiation to protect this adhesive joint.

4. The device as claimed in claim 1, wherein the metallic track has a function of providing protection against the UV radiation for an adhesive joint used for the assembly of the panel and the support frame, and a function of detecting a crack in the panel, by being in the form of the open loop and by being electrically connected to the electrical continuity detector.

5. The device as claimed in claim 1, the support frame being assembled onto a casing containing the reflector, with the interposition of a seal.

6. The device as claimed in claim 1, the UV detector being carried on an electronic circuit card positioned above the reflector.

7. The device as claimed in any of claim 1, comprising a radiator supporting the reflector, this radiator having grooves which are formed between fins and which accommodate tubes for the circulation of a cooling liquid.

8. The device as claimed in claim 7, the tubes being retained by clamps fitted between the fins.

9. The device as claimed in claim 1, comprising a control circuit which stores a log of the UV emission of the flashes, based on the radiation detected by the UV detector.

10. The device as claimed in claim 1, the reflector being fixed on the radiator with the interposition of a conductive sheet having a thermal conductivity greater than or equal to 2 W/m·K.

11. The device as claimed in claim 10, the tubes being inserted at their ends into manifolds having seals fitted on the tubes.

12. The device as claimed in claim 11, the manifolds also accommodating the ends of the flash lamp.

13. The device as claimed in claim 11, the flash lamp being accommodated in a quartz envelope engaged in the manifolds.

14. A Method comprising using the device as claimed in claim 1 for destroying pathogenic or undesirable agents.

15. The Method as claimed in claim 14, wherein foods, fruit or vegetables, are exposed to the UV radiation.

16. The Method as claimed in claim 14, wherein the dose of UV radiation emitted by the lamp is measured at each flash, using the aforesaid UV detector.

17. The Method as claimed in claim 14, wherein information related to the UV emission of each flash is stored.

18. The Method as claimed in claim 14, wherein the energy sent to the lamp is modified on the basis of the previously measured radiation emitted by the lamp, to compensate for the variation of the emission characteristics caused by the aging of the lamp.

19. The Method as claimed in claim 14, the electrical continuity of the metallic track extending along the at least one longer side of the panel being measured before and/or after the emission of each flash.

20. The device as claimed in claim 1, the flash lamp being contained in an enclosure, and the latter containing a substance absorbing the atmospheric oxygen present in the enclosure.

21. The device as claimed in claim 20, said substance comprising an iron compound, in powder form packaged in sachets.

22. A method for destroying pathogenic agents present on the surfaces of objects such as fruit or vegetables, comprising causing the rotation of the objects to be treated through more than 360°, subjecting the surfaces of the objects thus rotated to a UVC-rich light with a device as claimed in claim 1, the energy density of the flash or flashes being such that the surfaces of the objects are exposed to an energy density of at least 1 $J/cm^2$ and to a power density of at least 2 $kW/cm^2$, and that at least 20% of the received energy is between 200 and 315 nm.

23. The method as claimed in claim 22, the objects resting on a conveyer comprising rollers moving with the objects, the rollers being made to rotate, at least when they pass under the light emission windows, the rollers coming into contact with a friction strip which causes them to revolve thereon, or being fixed to toothed wheels which engage with a toothed belt or a chain extending under the emission window or windows.

24. The device as claimed in claim 1, the reflector comprising an opening, and the UV detector being placed behind the opening.

25. The device as claimed in claim 24, the diameter of the opening being less than or equal to 5 mm.

* * * * *